United States Patent
Jau et al.

(10) Patent No.: US 6,881,956 B1
(45) Date of Patent: Apr. 19, 2005

(54) METHOD AND APPARATUS FOR SCANNING SEMICONDUCTOR WAFERS USING A SCANNING ELECTRON MICROSCOPE

(75) Inventors: Jack Y. Jau, Los Altos, CA (US); Zhongwei Chen, San Jose, CA (US)

(73) Assignee: Hermes-Microvision, Inc., Hsinchu (TW)

( * ) Notice: Subject to any disclaimer, the term of this patent is extended or adjusted under 35 U.S.C. 154(b) by 0 days.

(21) Appl. No.: 10/649,599

(22) Filed: Aug. 26, 2003

Related U.S. Application Data

(63) Continuation of application No. 09/668,697, filed on Sep. 22, 2000, now Pat. No. 6,710,342.

(51) Int. Cl.$^7$ ............................................. G01N 23/04
(52) U.S. Cl. ..................... 250/311; 250/310; 250/306; 250/307; 250/491.1
(58) Field of Search ................................ 250/310, 311, 250/306, 307, 49.1

(56) References Cited

U.S. PATENT DOCUMENTS

| | | |
|---|---|---|
| 4,449,051 A * | 5/1984 | Berkowitz ............... 250/492.2 |
| 4,833,323 A | 5/1989 | Scholze |
| 5,497,007 A | 3/1996 | Uritsky et al. |
| 5,502,306 A | 3/1996 | Meisburger et al. |
| 5,578,821 A | 11/1996 | Meisberget et al. |
| 6,038,018 A | 3/2000 | Yamazaki et al. |
| 6,084,679 A | 7/2000 | Steffan et al. |
| 6,087,673 A | 7/2000 | Shishido et al. |
| 6,218,664 B1 | 4/2001 | Krans et al. |
| 6,392,231 B1 | 5/2002 | Chen |
| 6,710,342 B1 * | 3/2004 | Jau et al. ............... 250/311 |
| 2004/0195522 A1 * | 10/2004 | Winkler et al. ........ 250/441.11 |

\* cited by examiner

Primary Examiner—Frank G. Font
Assistant Examiner—James P. Hughes
(74) Attorney, Agent, or Firm—Townsend and Townsend and Crew LLP

(57) ABSTRACT

An apparatus and method for scanning the surface of a specimen is disclosed for defect inspection purposes. Scanning Electron Microscope (SEM) is used to scan the surface of a specimen. The scanning method employed by the SEM comprises the steps of: generating a particle beam from a particle beam emitter, and scanning the surface of the specimen by bending the particle beam at an angle with respect to the surface of the specimen, wherein the particle beam traverses an angle that is not parallel or perpendicular to the orientation of the specimen. The specimen being scanned is a semiconductor wafer or a photomask.

20 Claims, 4 Drawing Sheets

METHOD AND APPARATUS FOR SCANNING SEMICONDUCTOR WAFERS USING A SCANNING ELECTRON MICROSCOPE

CROSS REFERENCES TO RELATED APPLICATIONS

This present application is a con of U.S. application Ser. No. 09/668,697 filed Sep. 22, 2000, now U.S. Pat No. 6,710,342 commonly owned and hereby incorporated by reference for all purposes.

FIELD OF THE INVENTION

This invention relates generally to Scanning Electron Microscope (SEM)-based scanning of specimens and, more particularly, to a SEM based method of scanning of semi-conductor for defect inspection, and to a SEM-based method of scanning photo mask for defect inspection.

BACKGROUND OF THE INVENTION

Scanning methods of different kinds are used in applications that involve inspection of very small structures of objects in great detail. Some of these applications include defect review and inspection of specimens such as very large scale integrated (VLSI) circuits, wafers, or other articles, critical dimensioning of features in these specimens as well as design and process verification of the specimens. In such applications, scanning electron microscopes (SEM) are typically employed for scanning the specimens.

Scanning electron microscopes use an electron beam to scan the specimen. A SEM makes use of the wave nature of electrons to produce images with high resolution. A SEM operates by generating a beam of electrons called a particle beam. The particle beam is collimated by condenser lenses of the SEM and focused on the surface of the specimen through an objective lens system. The focused particle beam is deflected with the help of a deflection system of the SEM. The deflection system helps in moving the focused particle beam across the surface of the specimen in a particular direction for purposes of scanning. The deflected particle beam collides with specimen and generates secondary electrons (SE) and back-scattered electrons (BSE). The SE and BSE are then captured by a detector system of the SEM to produce an image of the specimen. The produced image is useful in inspecting the minute structures of the specimen under examination in great detail.

According to conventional SEM scanning methods for wafer inspection, the particle beam is first focused on the wafer and is then deflected either in parallel or perpendicular direction orientation with respect to the die orientation of the wafer. However, such a parallel or perpendicular direction of the deflected particle beam does not help in overcoming the edge effect or aliasing effect, which commonly occurs when scanning the patterned structures on a semiconductor wafer. Aliasing effect refers to the situation where the image lines appear to have jagged edges. During wafer scanning, aliasing may be caused by a slight misalignment between the die orientation or the particle beam scanning direction, thus resulting in an apparent detection of non-uniformity along the edges of the patterned structure on the surface of the wafer by a detector system. This leads to an otherwise satisfactory wafer being categorized as faulty.

SUMMARY OF THE INVENTION

It is therefore a goal of the invention to provide a method in reducing the edge effect or aliasing effect in wafer inspections.

The aforementioned and related drawbacks associated with conventional SEM and methods of scanning specimens using a SEM are substantially reduced or eliminated by the present invention. The present invention is directed to a SEM, which scans the surface of a semiconductor wafer by performing the following steps: generating a particle beam from a particle beam emitter; and scanning the surface of the semiconductor wafer by deflecting the particle beam to a direction relative to the die orientation, such that the particle beam traverses a direction that is neither parallel nor perpendicular to the die orientation of the semiconductor wafer. According to the present invention, the particle beam is deflected onto the surface of the semiconductor so as to scan the surface of the semiconductor wafer at an angle within the preferred ranges of (1° and 89°) or (91 and 179°) or (−89° and −1°) or (−179° and −91°) with respect to the die orientation. According to the present invention, the SEM comprises: a particle beam emitter for emitting a particle beam in a SEM; and a deflective unit operative to scan the surface of the semiconductor wafer by deflecting the particle beam at an angle relative to the die orientation of the semiconductor wafer, such that the particle beam traverses a direction that is not parallel or perpendicular to the orientation of the die on the semiconductor wafer.

An advantage of the present invention is that the non-parallel and non-perpendicular scanning angles reduce aliasing effects.

Another advantage of the present invention is that the non-parallel and non-perpendicular scanning angles can be easily implemented with current scanning electron microscopes.

BRIEF DESCRIPTION OF THE DRAWINGS

The aforementioned and other advantages and features of the present invention will become better understood upon reviewing the following detailed description of the invention taken in conjunction with the following drawings, where like numerals represent like elements, in which.

DETAILED DESCRIPTION OF THE INVENTION

Figure 1:
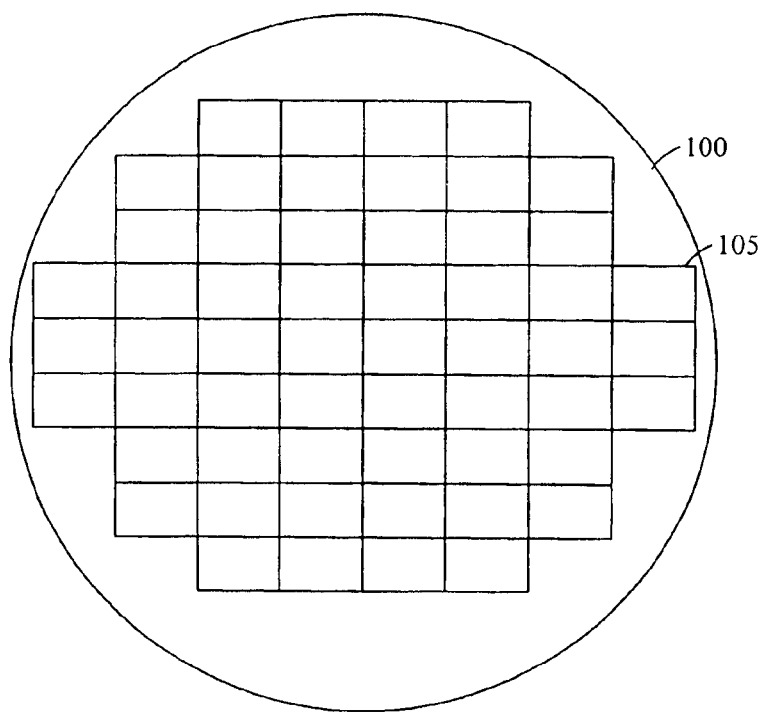
FIG. 1 is a diagram illustrating a conventional semiconductor wafer having a plurality of die formed thereon.

The SEM and method of operation thereof will now be described with reference to FIGS. 1 to 6d. FIG. 1 is a diagram illustrating a conventional wafer 100 with a plurality of dies 105 formed thereon. In practice, each of the die 105 has electronic circuitries (not shown) formed thereon. The underlying circuitries are fabricated by a series of patterned structures of interconnected lines (conducting and semiconducting) and interconnects formed on the surface of a semiconductor wafer. Each of these lines and corresponding interconnects of the circuitry is generally provided with either a parallel or perpendicular orientation with respect to the die orientation.

Figure 2A:
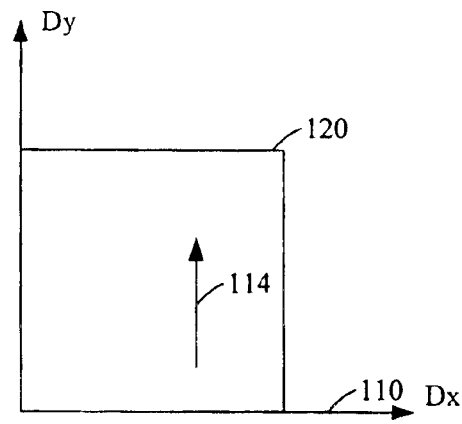
FIGS. 2a and 2b are graphs illustrating a die orientation versus SEM scanning angle according to conventional methods of wafer scanning.
Figure 2B:
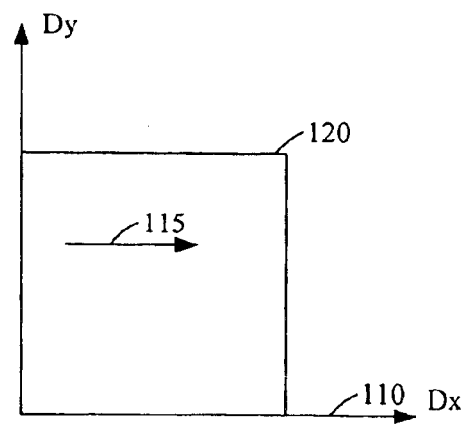

FIGS. 2a and 2b are graphs illustrating die orientation 110 versus SEM scanning angle 115 according to conventional methods of wafer scanning. FIG. 2a illustrates the scanning angle 115 being perpendicular to the orientation of a die 120 on a semiconductor wafer. FIG. 2b illustrates the scanning angle 115 being parallel to the orientation of a die 120. This is according to conventional means of scanning employed in wafer inspection that require aligning the scan direction of particle beam 125 (shown in FIG. 3) in a parallel or perpendicular orientation with respect to the die orientation 110 because integrated circuit structures are generally fabricated either in a parallel or perpendicular orientation with respect to the die orientation on a semiconductor wafer.

Figure 3:
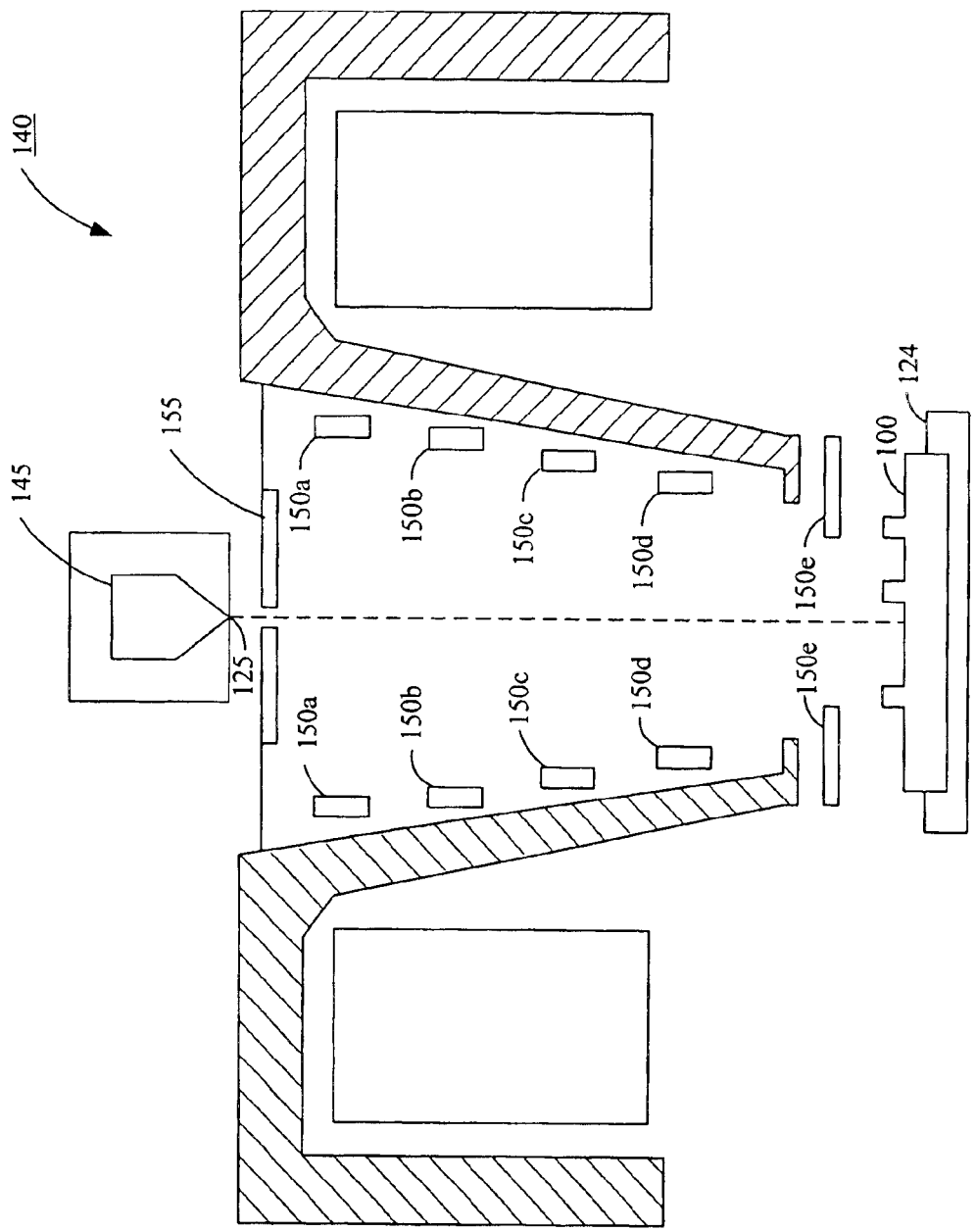
FIG. 3 is an illustration of a particle beam being incidental on the surface of a specimen.

FIG. 3 is a diagram illustrating a particle beam 125 being incidental on the surface of a semiconductor wafer 100 that is supported by a holder 124. Conventionally, a SEM 140 comprises of a particle beam emitter 145 operative to emit a particle beam 125. The particle beam 125 is passed across the surface of the semiconductor wafer 100 in either a parallel or perpendicular manner with respect to the die orientation as illustrated in FIGS. 2a and 2b respectively.

According to conventional wafer scanning methods, a slight shift in the orientation of the particle beam during scanning will result in the apparent detection of an irregularity along the edge of the patterned structure of the die on the semiconductor wafer 100 by a detector system 155. During wafer inspection, this will result in an otherwise satisfactory wafer being categorized as flawed.

Figure 4A:
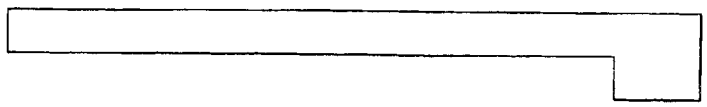
FIG. 4a is a diagram illustrating an exemplary patterned structure on a semiconductor wafer.

Referring now to FIG. 4a, which shows an example of a typical patterned surface structure on a semoconductor wafer.

Figure 4B:
FIG. 4b is an illustration of the patterned structure showing aliasing effect in its image.

FIG. 4b is an illustration of how aliasing negatively affects the image of the semiconductor wafer patterned structure provided by the detector system 155 correspond to the structure shown in FIG. 4a. Aliasing occurs during scanning of the wafer and is caused by a slight misalignment between the scanning direction of the particle beam and the physical orientation of the patterned circuit structure on the semiconductor wafer surface thus resulting in the detection of a non-uniformity along the edge of the surface patterned structure by the detector system 155. Consequently, the resulting image displays jagged edges 250 along the patterned structure and causes an otherwise satisfactory wafer to be categorized as faulty.

Figure 5:
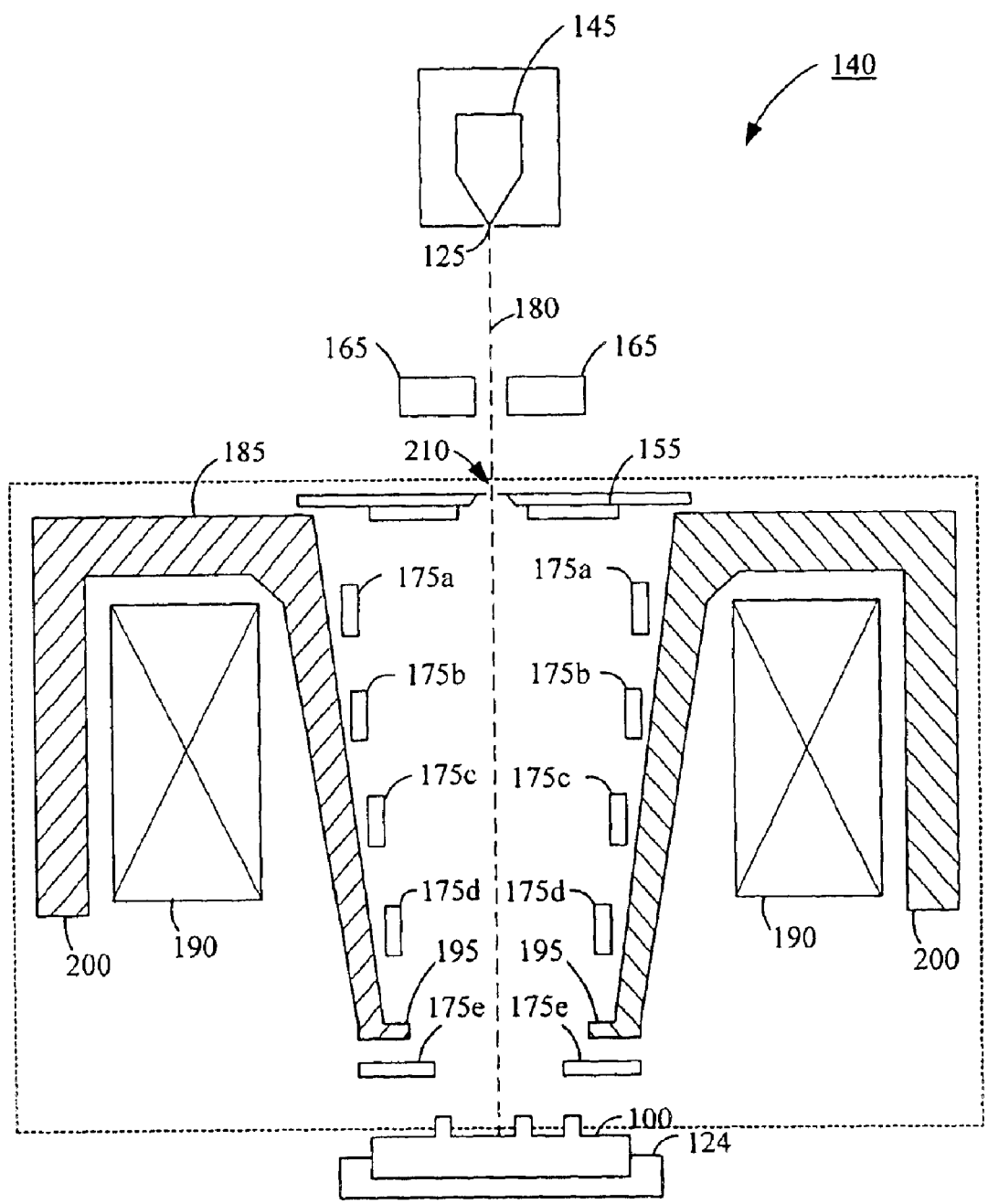
FIG. 5 is a diagram illustrating a cross-sectional view of an embodiment of a scanning electron microscope in accordance with a preferred embodiment of the present invention.

FIG. 5 is a diagram illustrating a cross-sectional view of an exemplary embodiment of a scanning electron microscope 140 in accordance with a preferred embodiment of the present invention. In this embodiment, SEM 140 comprises a particle beam emitter 145 (i.e., the effective source point for the particles) emitting a particle beam 125, an anode 165, an objective lens system 160 having a magnetic lens called a side pole lens composed of magnetic material 185 and exciting coils 190, and a plurality of deflection units 175a–175e. In a preferred embodiment, the particle beam is an electron beam and travels along a beam axis 180 between the particle beam source 145 and the semiconductor wafer 100. Typically, the specimen is a semiconductor wafer having feature sizes of about 0.05 μm to 0.20 μm or larger. An objective lens system 160 in the SEM 140 focuses the particle beam 125 into a small spot on the surface of the specimen, which is traversed over the semiconductor wafer 120 to be studied. The magnetic lens includes magnetic material 185 and exciting coils 190 for providing magneto-motive force to a magnetic circuit having field lines through the magnetic material and between the pole pieces 195 and 200. The central bore of the magnetic lens has the shape of a circular bucket, which is axially symmetric about the beam axis 180. At the place where the primary particle beam 125 enters the objective lens system 160, through a beam-defining aperture 210. The beam-defining aperture 210 determines the size of the particle beam 125 allowed to enter the objective lens system 160 and in one embodiment confines the beam diameter to about 0.1 μm. A lens pole piece at the point where the primary particle beam 125 exits the magnetic lens is circumscribed by pole pieces 195 and 200. A more detailed description of the SEM and its method of operation is present in co-pending patent application Ser. No. 09/513,306 entitled "Swinging Objective Retarding Immersion Lens Electron Optics Focusing, Deflection and Signal Collection System and Method" and assigned to the assignee of the present invention is fully incorporated herein.

Immediately below the beam defining aperture 210 is an annular detector system 155 which collects secondary electrons (SE) and back scattered electrons (BSE) emitted from the semiconductor wafer 100 during the scanning operation. Detector system 155 has an aperture that is larger than the beam defining aperture 210 so the particles from the primary beam 125 are not affected in any way by the detector system 155 as they pass through the beam defining aperture 210.

Residing in the central bore are deflection units 175a–175d. These units are disk-shaped rings, which are axially symmetric about the Z-axis. Located outside of the central bore is deflection unit 175e, which is co-axial with the Z-axis and similar in construction to the deflection units within the central bore of the objective lens system. In accordance with the present invention, a first set of deflection units 175a, 175d and 175e deflect the particle beam spot a deflection field distance of about 600 μm in one version of the invention upon application of an appropriate voltage to the exciting coils 190. A second set of deflection units 175b and 175c is dedicated to producing a more rapid scanning movement of the beam to cover an area of approximately 50 μm, and is centered on the position determined by the first set of deflection units 175a, 175d and 175e. Scanning is performed by dwelling on a point for a period of time (on the order of a few or tens of nanoseconds), moving to the next point in a row of points and then repeating the scan operation for the next row until an entire grid of points covering the area is scanned. If the beam spot rests at a position on the semiconductor wafer for 10 ns then a single scan of a 50 μm line requires about 5 μs and the scan of the entire area takes at least 2.5 ms. In practice, an additional amount of time (about 1 μs/scan line) is required for retracing the beam between each successive scan causing the total time to scan the field to be about 3 ms (2.5 ms+500×1 μs). Deflection unit 175e is particularly important for improving the size of the deflection field over the semiconductor wafer 100 because it is closest to the specimen and in the retarding field produced by the deflection. Thus deflection unit 175e will have a large effect on the position of the particle beam 125 because it is deflecting a beam with much lower energy than the deflection units 175a–175d and it is the deflection unit nearest the landing point of the beam on the specimen. On traversing across the surface of the semiconductor wafer 100, the particle beam 125 is deflected by deflection units 175a–175e and captured by a detector system 155. These captured electrons are called secondary electrons or back scattered electrons and are different from the primary electrons forming the particle beam 125 incidental on the surface of the semiconductor wafer 100. Once the secondary electrons and the back-scattered electrons are captured by the detector system 155, an image of the scanned semiconductor wafer is reconstructed. This image can then be used for wafer inspection to detect defects in the wafer in great detail.

Now referring to FIGS. 6a–6d, according to the present invention, the scanning direction vector S used is neither parallel nor perpendicular to the die orientation on the surface of the semiconductor wafer. This is achieved by deflecting the particle beam at an angle in any of the ranges not including 90°, 180° or 270°. In accordance with preferred embodiments of the present invention, scanning angles within the ranges of (1° and 89°) or (91° and 179°) or (–89° and –1) or (–179° and –91°) relative to the die orientation vector Dx are used. In accordance with the present invention, the preferred ranges of scanning angles are (15° and 75°), (105° and 165°), (–105° and –165°), (–15° and –75°).

Figure 6A:
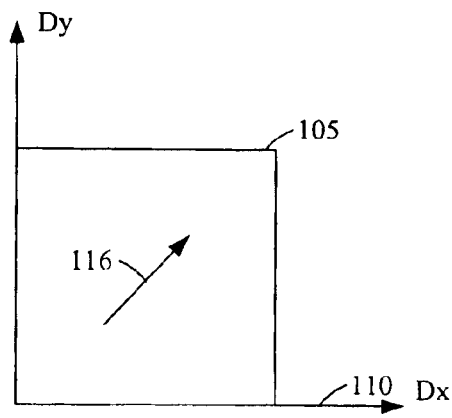
FIG. 6a is an illustration of a preferred embodiment of the present invention where the scanning direction vector lies at an angle within the range of 1° and 89° relative to the die orientation of the specimen.

FIG. 6a is an illustration of a first embodiment of the present invention where the scanning direction vector S 116 lies at an angle within the range of 1° and 89° relative to the die orientation of the semiconductor wafer.

Figure 6B:
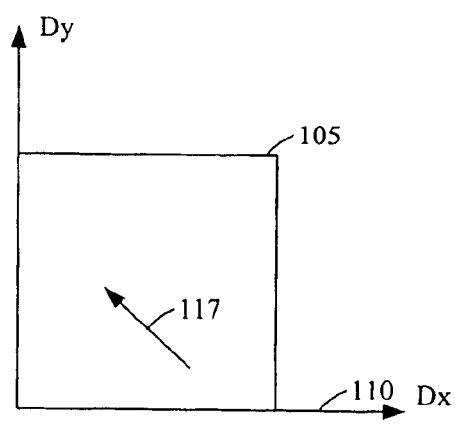
FIG. 6b is an illustration of a preferred embodiment of the present invention where the scanning direction vector is at an angle within the range of 91° and 179° relative to the die orientation of the specimen.

FIG. 6b is an illustration of a second embodiment of the present invention where the scanning direction vector S 117 is at an angle within the range of 91° and 179° relative to the die orientation of the semiconductor wafer.

Figure 6C:
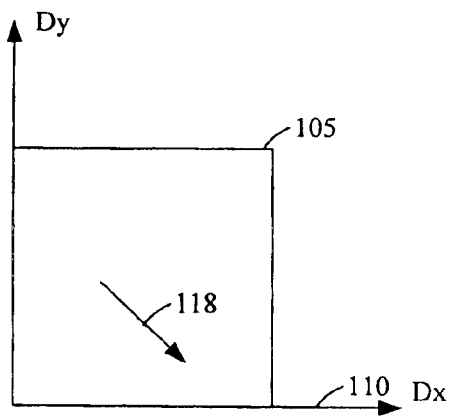
FIG. 6c is an illustration of a preferred embodiment of the present invention where the scanning direction vector is at an angle within the range of −89° and −1° relative to the die orientation of the specimen.

FIG. 6c is an illustration of a third embodiment of the present invention where the scanning direction vector S 118 is at an angle within the range of –89° and –1° relative to the die orientation of the semiconductor wafer.

Figure 6D:
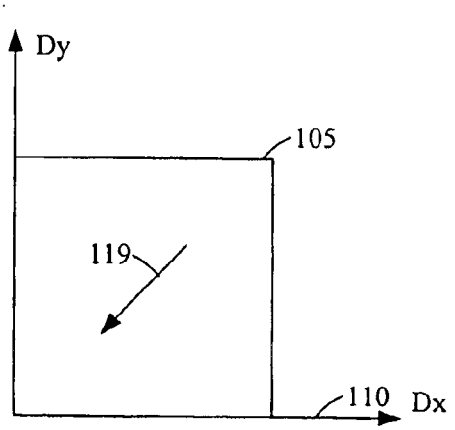
FIG. 6d is an illustration of a preferred embodiment of the present invention where the scanning direction vector is at an angle within the range of −179° and −91° relative to the die orientation of the specimen.

FIG. 6d is an illustration of a fourth embodiment of the present invention where the scanning direction vector S 119 is at an angle within the range of –179° and –91° relative to the die orientation of the semiconductor wafer.

Anti-aliasing is the name for techniques designed to reduce or eliminate aliasing in the image of a surface structure on a semiconductor wafer. As discussed earlier, aliasing is caused by a slight misalignment between the particle beam scanning direction and resulting in the detection of an apparent irregularity along the edge of a surface structure on of the semiconductor wafer. By scanning the surface of the semiconductor wafer at an angle within the preferred ranges as provided above, the negative effects caused by aliasing are minimized thus producing images with much better quality along the edge of a structure.

Whereas the present invention may be embodied in many forms, details of a preferred embodiment are schematically shown in FIGS. 1 through 6d, with the understanding that the present disclosure is not intended to limit the invention to the embodiment illustrated. While the invention has been particularly shown and described with reference to certain embodiments, it will be understood by those skilled in the art that various alterations and modifications in form and detail may be made therein. Accordingly, it is intended that the following claims cover all such alterations and modifications as fall within the true spirit and scope of the invention.

What is claimed is:

1. An apparatus for scanning the surface of a specimen, using a Scanning Electron Microscope comprising:
   a particle beam emitter for emitting a particle beam in a SEM; and
   a deflection unit operative to scan the surface of the specimen by bending the particle beam at an angle relative to the orientation of the specimen, such that the particle beam traverses an angle that is not parallel or perpendicular to the orientation of the specimen.

2. An apparatus as recited in claim 1, further comprising:
   a detector system for collecting the back scattered electrons deflected after traversing across the surface of the specimen.

3. An apparatus as recited in claim 1, wherein the specimen being scanned is a semiconductor wafer.

4. An apparatus as recited in claim 1, wherein the deflection unit deflects the particle beam at an angle relative to the orientation of the specimen in response to the application of an appropriate voltage potential to the particle beam deflecting means.

5. An apparatus as recited in claim 1, wherein the deflection unit deflects the particle beam at an angle relative to the die orientation within a range of 1° and 89°.

6. An apparatus as recited in claim 5, wherein the deflection unit deflects the particle beam at an angle relative to the die orientation within the range of 15° and 75°.

7. An apparatus as recited in claim 1, wherein the deflection unit deflects the particle beam at an angle relative to the die orientation within a range of 91° and 179°.

8. An apparatus as recited in claim 7, wherein the deflection unit deflects the particle beam at an angle relative to the die orientation within the range of 105° and 165°.

9. An apparatus as recited in claim 1, wherein the deflection unit deflects the particle beam at an angle relative to the die orientation within a range of –179° and –91°.

10. An apparatus as recited in claim 9, wherein the deflection unit deflects the particle beam at an angle relative to the die orientation within the range of –105° and –165°.

11. An apparatus as recited in claim 1, wherein the deflection unit deflects the particle beam at an angle relative to the die orientation within a range of –89° and –1°.

12. An apparatus as recited in claim 11, wherein the deflection unit deflects the particle beam at an angle relative to the die orientation within the range of –15° and –75°.

13. An apparatus for scanning the surface of a specimen, using a Scanning Electron Microscope comprising:
   a magnetic lens for generating a magnetic field in the vicinity of the specimen to focus the particles of the particle beam on the specimen, the magnetic lens having a central bore through which the particle beam travels;
   an electrode having a potential for providing a retarding field to the particle beam near and at the specimen to reduce the energy of the particle beam when the beam collides with the specimen;
   a deflection system including a plurality of deflection units situated along the beam axis for deflecting the particle beam to allow scanning of the specimen, at least one of the deflection units located in the retarding field of the beam, the remainder of the deflection units located within the central bore of the magnetic lens, the deflection system operative to scan the surface of the specimen by bending the particle beam at an angle relative to the orientation of the specimen, such that the particle beam traverses an angle that is not parallel or perpendicular to the orientation of the specimen; and wherein the specimen being scanned is a semiconductor wafer.

14. An apparatus as recited in claim 13, further comprising:

a detector system for collecting the back scattered electrons deflected after traversing across the surface of the specimen.

15. An apparatus as recited in claim 13, wherein the deflection unit deflects the particle beam at an angle relative to the orientation of the specimen in response to the application of an appropriate voltage potential to the particle beam deflecting means.

16. An apparatus as recited in claim 13, wherein the deflection unit deflects the particle beam at an angle relative to the die orientation within a range of 1° and 89°.

17. An apparatus as recited in claim 13, wherein the deflection unit deflects the particle beam at an angle relative to the die orientation within a range of 91° and 179°.

18. An apparatus as recited in claim 13, wherein the deflection unit deflects the particle beam at an angle relative to the die orientation within a range of −179° and −91°.

19. An apparatus as recited in claim 13, wherein the deflection unit deflects the particle beam at an angle relative to the die orientation within a range of −89° and −1°.

20. An apparatus for scanning the surface of a specimen, using a Scanning Electron Microscope comprising:

a magnetic lens for generating a magnetic field in the vicinity of the specimen to focus the particles of the particle beam on the specimen, the magnetic lens having a central bore through which the particle beam travels;

an electrode having a potential for providing a retarding field to the particle beam near and at the specimen to reduce the energy of the particle beam when the beam collides with the specimen;

a deflection system including a plurality of deflection units situated along the beam axis for deflecting the particle beam to allow scanning of the specimen, at least one of the deflection units located in the retarding field of the beam, the remainder of the deflection units located within the central bore of the magnetic lens, the deflection system operative to scan the surface of the specimen by bending the particle beam at an angle relative to the orientation of the specimen, such that the particle beam traverses an angle that is not parallel or perpendicular to the orientation of the specimen; and a detector system for collecting the back scattered electrons deflected after traversing across the surface of the specimen.

* * * * *